United States Patent [19]

Foguet et al.

[11] Patent Number: 4,859,675
[45] Date of Patent: Aug. 22, 1989

[54] 1-[2-(PHENYLMETHYL)PHENYL]PIPERAZINES AS ANTIDEPRESSANTS

[75] Inventors: Rafael Foguet; Ernesto Forne; Aurelio Sacristan; José A. Ortiz, all of Barcelona, Spain

[73] Assignee: Ferrer Internacional S.A., Barcelona, Spain

[21] Appl. No.: 207,375

[22] Filed: Jun. 15, 1988

[30] Foreign Application Priority Data

Jul. 29, 1987 [ES] Spain .................................... 8702460

[51] Int. Cl.$^4$ .................... A61K 31/495; C07D 295/02
[52] U.S. Cl. ...................................... 514/255; 544/395
[58] Field of Search ........................ 544/395; 514/255

[56] References Cited

U.S. PATENT DOCUMENTS 4,194,049  3/1980  Field et al. ...................... 548/342

OTHER PUBLICATIONS

Wolf Dieter Zahler et al, Chem. Ber. 96, 765(1963).
Gassman et al, J.A.C.S. 100(24), 7600(1978).

Primary Examiner—Anton H. Sutto
Assistant Examiner—Cecilia Shen
Attorney, Agent, or Firm—Michael J. Striker

[57] ABSTRACT

An 1-[2-(phenylmethyl)phenyl]piperazine of the formula (I),

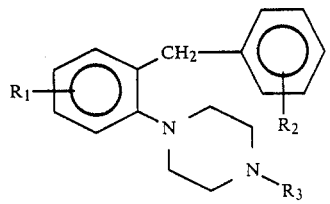

or a pharmaceutically acceptable acid addition salt thereof, wherein $R_1$ is hydrogen, $C_{1-4}$ alkyl or halogen, $R_2$ is hydrogen, $C_{1-4}$ alkyl, halogen or $C_{1-4}$ alkoxy and $R_3$ is hydrogen or methyl.

such compounds are useful as antidepressive agents.

5 Claims, No Drawings

1-[2-(PHENYLMETHYL) PHENYL]PIPERAZINES AS ANTIDEPRESSANTS

BACKGROUND OF THE INVENTION

The present invention relates to novel and therapeutically valuable 1-[2-(phenylmethyl)phenyl]piperazines, its pharmaceutically acceptable acid addition salts, and the method for preparing the same.

SUMMARY OF THE INVENTION

As a result of intensive investigations to develop therapeutically useful compounds, the present inventors have found that novel 1-[2-(phenylmethyl)phenyl]piperazines and pharmaceutically acceptable acid addition salts thereof exhibit outstanding antidepressive activity.

DETAILED DESCRIPTION OF THE INVENTION

The 1-[2-(phenylmethyl)phenyl]piperazines of the present invention are represented by the following formula (I):

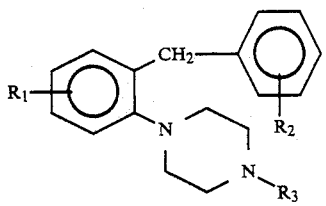

In the above aformula, $R_1$ is hydrogen, $C_{1-4}$ alkyl or halogen, $R_2$ is hydrogen, $C_{1-4}$ alkyl, halogen or $C_{1-4}$ alkoxy and $R_3$ is hydrogen or methyl.

The compounds of formula (I) are prepared according to the following scheme:

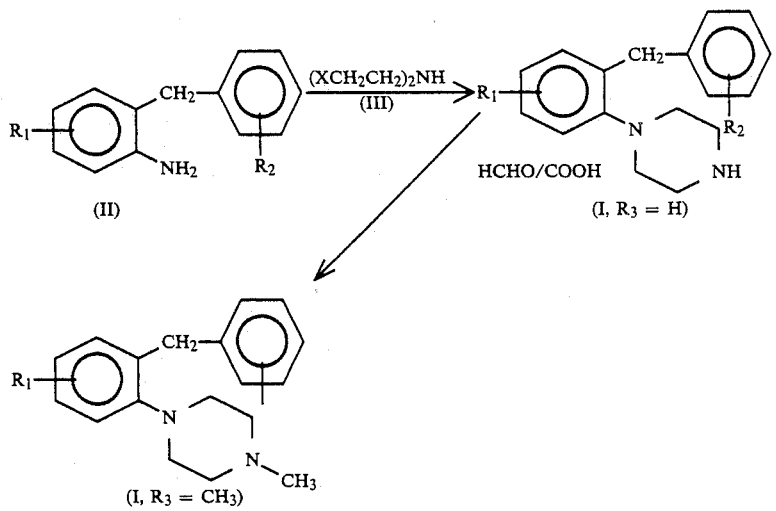

In the starting compounds of general formula (II), $R_1$ and $R_2$ are as defined above. In (III), X represents chlorine or bromine.

The preparation of the starting compounds of general formula (II) is carried out, from the corresponding 2-aminobenzophenones, either (a) by direct reduction using hydrazine under the conditions of Wolff-Kishner's reaction (M. Gall et al: J. Med. Chem., 19(8), 1057, 1976; W. D. Zahler et al: Ber., 96, 765, 1963; H. H. Oelschläger et al: Arzn.-Forsch., 23(6), 802, 1973) or sodium and ethanol (E. J. Engels et al: J. Chem. Soc., 2694, 1959), or (b) by reduction with zinc and hydrochloric acid from the corresponding carbinols (Hoffmann-La Roche: U.S. Pat. No. 4,194,049, 1980) or (c) directly from the substituted anilines (P. S. Gassman et al: J. Am. Chem. Soc., 100(24), 7600, 1978; P. G. Gassman et al: J. C. S. Chem. Comun., 488, 1973).

The piperazine ring is formed, according to the above scheme, from respective starting 2-(phenylmethyl)anilines (II) and bis-(2-haloethyl)amines (III) in the presence of basic coadjuvants. Suitable basic coadjuvants are alkaline or alkaline earth carbonates or bicarbonates. $C_{1-4}$ alcohols or $C_{4-6}$ alkoxyethanols are used as suitable solvents.

The N-methylated homologues (I, $R_3=CH_3$) are obtained from (I, $R_3=H$) by Eschweiler-Clarde's reaction using formaldehyde and formic acid.

The compounds of the present invention are extremely useful in Human Therapeutics due to their outstanding antidepressive activity. The compounds may be administered, mixed with suitable carriers, orally in the form of tablets, coated-tablets, capsules, powder, syrup, solution, etc., and by injection at daily doses ranging from 0.1 to 10 mg/kg.

The following examples will illustrate the present invention in more detail, but they are not to be construed as limiting the present invention.

EXAMPLE 1

1-[2-(Phenylmethyl)phenyl]piperazine hydrochloride

In a flask fitted with stirrer and cooler, 18.33 g (0.1 mole) of 2-benzylaniline and 17.85 g (0.1 mole) of bis-(2-chloroethylamine)hydrochloride are dissolved in 100 ml of n-butanol and refluxed for 8 hours in an oil bath. The mixture is then allowed to cool, and 6.91 g (0.05 mole) of anhydrous potassium carbonate are added under reflux for 8 hours; the addition of 6.91 g of anhydrous potassium carbonate under 8-hour reflux ws repeated twice. It is then allowed to cool, the insoluble salts are filtered and the butyl alcohol solution is evaporated to dryness in vacuo. The resinous residue is dissolved in 100 ml of methylene chloride, a stream of hydrochloric acid gas with cooling is bubbled into, and the hydrochloride precipitates by adding ethyl ether; it is then filtered and dried to give 28 g of a slightly coloured solid. 10.36 g (37%) of end product as a whitish solid, m.p. 192°-194° C. were obtained by recrystallization from acetonitrile.

IR Spectrum (KBr), cm$^{-1}$: 3350, 3100-2440, 1490, 1230, 930, 765.

$^1$H—NMR Spectrum (d$_6$-DMSO) ppm: 3.1 (two symmetric bands, 8H; piperazine), 4.0 (s, 2H; Ar—C$\underline{H}_2$—Ar), 7.2 (m, 9H, Ar—) and 9.8 (wide, 2H; —N$^+$H$_2$).

EXAMPLE 2

1-[2-(Phenylmethyl)phenyl]-4-methylpiperazine hydrochloride

A mixture of 3.46 g of 1-[2-(phenylmethyl)phenyl]-piperazine hydrochloride, 2.5 ml of 38% formaldehyde and 1 ml of formic acid is heated in an oil bath at 110°-120° C. for 2 hrs. It is then concentrated on a rotatory evaporator to give, after dried, 3.64 g of purified yellowish solid of m.p. 202°-204° C. with analysis correct.

IR Spectrum (KBr), cm$^{-1}$: 3400, 3060-2400, 1480, 1225, 1020, 750.

$^1$H—NMR Spectrum (d$_6$-DMSO), ppm: 2.80 (d, 3H, J=4 Hz; N—CH$_3$), 3.25 (two symmetric bands, 8H; piperazine), 4.0 (s, 2H; Ar—C$\underline{H}_2$—Ar), 7.25 (m, 9H; Ar—) and 9.60 (wide, 1H; —N$^+\underline{H}$—).

EXAMPLE 3

1-[4-Chloro-2-(phenylmethyl)phenyl]piperazine hydrochloride (a) 42.14 g of 2-benzyl-4-chloroaniline, 35.52 g of bis-(2-chloroethylamine)hydrochloride in 190 ml of n-butanol and repeated additions of 13.35 g of anhydrous potassium carbonate are reated according to the method described in Ex. 1. After cooling, the insoluble material is filtered and washed over the same filter with 4×50 ml of methylene chloride (the insoluble residue, which is composed of inorganic salts, is rejected). The solvent is evaporated to give 30.8 g (50%) of a solid as hydrochloride. Recrystallization from isopropanol yields 21 g (34%) of white solid of mp. 209°-210° C. and analysis correct.

IR Spectrum (KBr), cm$^{-1}$: 3500, 3100-2450, 1590, 1480, 1450, 820, 720, 690.

$^1$H—NMR Spectrum (CDCl$_3$), ppm: 3.1 (twc symmetric bands, 8H; piperazine), 3.90 (s, 2H; Ar—C$\underline{H}_2$—Ar—), 7.15 (m, 8H, Ar—) and 9.75 (wide, 2$\overline{H}$; —NH$_2$).

(b) In a flask fitted with stirrer and cooler is placed 27.60 g of 2-benzyl-4-chloroaniline, 22.70 g of bis-(2-chloroethylamine), 80 ml of n-butoxyethanol, and 17.60 g of anhydrous potassium carbonate. The mixture is refluxed for 30 hrs in an oil bath; it is allowed to cool, poured onto 300 ml of water and extracted four times with 4×250 ml of ethyl acetate. The organic extracts are washes with 3×100 ml of 1M sodium hydroxide solution and salt-saturated water to neutralization, then dried and evaporated to give an oily residue (39 g). By silica gel column chromatography (methylene chloride/methanol with increasing polarity), 12.4 g (34%) of rose-coloured solid corresponding to the base are isolated with 4% CH$_3$OH, m.p. 68°-70° C. and analysis correct.

IR Spectrum (KBr), cm$^{-1}$: 3340, 3020-2740, 1475, 1445, 1130, 790, 695.

$^1$H—NMR Spectrum (CDCl$_3$), ppm: 2.87 (2m, symmetric, 8H; piperazine), 4.0 (s, 2H; Ar—C$\underline{H}_2$—Ar—) and 7.15 (m, 8H; Ar—).

EXAMPLE 4

1-[4-Chloro-2-(phenylmethyl)phenyl]-4-methylpiperazine hydrochloride

From 6.47 g of 1-[4-chloro-2-(phenylmethyl)phenyl]-piperazine hydrochloride, 4.18 ml of 38% formaldehyde and 1.68 ml of formic acid and operating as described in Ex. 2, 6.65 g of solid, are obtained, m.p. 207.5°-209° C. and analysis correct.

IR Spectrum (KBr), cm$^{-1}$: 3100-2400, 1475, 1445, 1105, 980, 735.

$^1$H—NMR Spectrum (d$_6$—DMSO), ppm: 2.75 (s, 3H; N—CH$_3$), 3.20 (wide, 8H; piperazine), 3.98 (s, 2H; Ar—CH$_2$—Ar—) and 7-7.4 (m, 8H, Ar—).

EXAMPLE 5

1-[5-Methyl-2-(phenylmethyl)phenyl]piperazine mono-, dihydrochloride (a) 39.52 g of 2-benzyl-4-methylaniline, 36.43 g of bis-(2-chloroethylamine) in 130 ml of n-butoxyethanol and 28.5 g of anhydrous potassium carbonate are reated according to the method described in Ex. 3 (b). By evaporation of the organic phase, an oily residue (58 g) is obtained which is then dissolved in dry methylene chloride and under cooling in a water-ice bath a stream of hydrochloric acid gas is bubbled into; the formed hydrochloride precipitates by adding dry ethyl ether (50 ml), and after one night in the refrigerator, it is filtered, washed with ethyl ether and dried. 34.0 g (55%) of the monohydrochloride as white solid of m.p. 202°-204° C. and chromatographically pure are obtained. By recrystallization from ethanol, white crystals of m.p. 209°-210° C. and analysis correct were obtained.

IR Spectrum (KBr), cm$^{-1}$: 3050-2400, 1585, 1495, 1440, 1230, 1130, 955, 730, 690.

$^1$H—NMR Spectrum (d$_6$—SMSO), ppm: 2.25 (s, 3H; CH$_3$—), 3.05 two symmetric bands, 8H; piperazine), 3.95 (s, 2H; Ar—CH$_2$—Ar), 6.9 (m, 3H; Ar—), 7.2 (s, 5H, Ar—) and 9.60 (wide, 2H, —N$^+$H$_2$—).

(b) 22.0 g of 1-[5-methyl-2-(phenylmethyl)phenyl]-piperazine, which are obtained by neutralization of its monohydrochloride with 1N sodium hydroxide dissolved in toluene, are dissolved in 130 ml of absolute ethanol. Hydrochlorid acid gas is bubbled into this solution with cooling in a water-ice bath until saturation and precipitation. The mixture is refluxed and dissolved in further 50 ml of ethanol; after cooling and filtering, 25 g of white crystals are obtained which correspond to the hydrochloride, m.p. 210°-212° C. and analysis correct.

IR Spectrum (KBr), cm$^{-1}$: 3400, 3100-2400, 1600, 1430, 1350, 1295, 1160, 1020, 910, 845, 745.

$^1$H—NMR (d$_6$—DMSO), ppm: 2.31 (s, 3H; CH$_3$—), 3.35 (wide band, 8H; piperazine), 4.15 (s, 2H; Ar—C$\underline{H}_2$—Ar), 7.03 (s), 7.2 (s, 8H; Ar—), 10.0 (wide, 2$\overline{H}$; —N$^+$H$_2$—) and 10.9 (s, 1H; —N$^+$H—).

EXAMPLE 6

1-[5-Methyl-2-(phenylmethyl)phenyl]piperazine hydrobromide, base (a) A mixture of 37.24 g of 2-benzyl-4-methylaniline in 215 ml of absolute ethanol and 61.98 g of bis-(2-bromo-ethylamine)hydrobromide is refluxed for 8 hours. It is allowed to cool, then 20.0 g of anhydrous sodium carbonate are added and refluxed for further 8 hours. After 24 hours in the refrigerator, it is filtered and the precipitate washed repeatedly with methylene chloride to 500-ml volume; the resulting solution is evaporated in vacuo to give 37.0 g (58%) of a yellowish solid corresponding to the hydrobromide, m.p. 220°–222° C., chromatographically pure and bromide analysis correct. Recrystallization from ethanol gave white crystals (80% yield), m.p. 227°–229° C. and analysis correct.

IR Spectrum (KBr), cm$^{-1}$: 3440, 3100–2400, 1580, 1500, 1445, 1235, 1135, 1080, 960, 800, 740, 700.

$^1$H—NMR Spectrum (CDCl$_3$), ppm: 2.3 (s, 3H; CH$_3$—), 3.17 (two symmetric bands, 8H; piperazine), 3.95 (s, 2H; Ar—CH$_2$—Ar—), 6.9–7.2 (multiple bands, 8H; Ar—) and 9.6 (wide, 2H; —N$^+$H$_2$—).

(b) 10.0 g of the hydrobromide as prepared in (a) are suspended in 100 ml of toluene and then neutralized with 1N sodium hydroxide while stirring for 30 minutes. The aqueous phase is decanted and the toluene phase is washed with water and neutralization; after evaporating, a residue of 8 g remains which is crystallized from 80 ml of hexane to give 5.07 g of white crystals, m.p. 64°–67° C., corresponding to the base, and analysis correct.

IR Spectrum (KBr), cm$^{-1}$: 3260, 3100–2800, 1490, 1450, 1135, 1110, 830, 735, 695.

$^1$H—NMR Spectrum (CDCl$_3$), ppm: 1.40 (s, 1H; —NH—), 2.26 (s, 3H; CH$_3$—), 2.84 (symmetric bands group, 8H; piperazine), 3.98 (s, 2H; Ar—CH$_2$—Ar—) and 6.6–7.1 (multiple bands, 8H; Ar—).

EXAMPLE 7

1-[5-Methyl-2-(phenylmethyl)phenyl]-4-methylpiperazine hydrochloride

From 5.20 g of 1-[5-methyl-2-(phenylmethyl)phenyl]-piperazine hydrochloride, 3.60 ml of 37% formaldehyde and 1.45 ml of formic acid and operating as described in Ex. 2, 5.25 g of white solid are obtained, m.p. 208°–211° C., chromatographically pure and analysis correct.

IR Spectrum (KBr), cm$^{-1}$: 3400, 3050–2400, 1500, 1450, 1255, 980, 745.

$^1$H—NMR (d$_6$-DMSO), ppm: 2.25 (s, 3H; CH$_3$—), 2.75 (s, 3H; N—CH$_3$), 3.17 (two symmetric bands, 8H; piperazine), 3.95 (s, 2H; Ar—CH$_2$—Ar) and 6.8–7.3 (multiple bands, 8H; Ar—).

EXAMPLE 8

1-[5-Chloro-2-(phenylmethyl)phenyl]piperazine hydrochloride 18.18 g of 2-benzyl-5-chloroaniline, 14.90 g of bis-(2-chloroethylamine)hydrochloride in 65 ml of n-butanol and repeated additions of 5.78 g of anhydrous potassium carbonate are reacted according to the method described in Ex. 1. The hydrochloride is formed in methylene chloride and a precipitate forms by adding ethyl ether; it is then filtered, washed repeatedly with ethyl ether and dried to give 17 g of hygroscopic product. 8.4 g (25%) of a whitish solid, m.p. 256°–258° C., chromatographically pure and elemental analysis correct are isolated by recrystallization from ethanol.

IR Spectrum (KBr), cm$^{-1}$: 3400, 3100–2400, 1550, 1450, 1235, 1040, 950, 860, 730, 695.

$^1$H—NMR Spectrum (d$_6$—DMSO), ppm: 3.07 (wide, 8H; piperazine), 3.95 (s, 2H; Ar—CH$_2$—Ar), 7–7.3 (m, 8H; Ar—) and 9.6 (wide, 2H; N$^+$H$_2$—).

EXAMPLE 9

1-[5-Chloro-2-(phenylmethyl)phenyl]-4-methylpiperazine hydrochloride

From 2.10 g of 1-[5-chloro-2-(phenylmethyl)phenyl]-piperazine hydrochloride, 1.36 ml of 37% formaldehyde and 0.55 ml of formic acid, and operating as described in Ex. 2, 2.2 g of whitish solid are isolated, m.p. 195°–197° C., chromatographically pure and analysis correct.

IR Spectrum (KBr), cm$^{-1}$: 3450, 3050–2400, 1500, 1470, 1240, 1010, 960, 755.

$^1$H—NMR Spectrum (CDCl$_3$), ppm: 2.85 (s, 3H, N—CH$_3$), 3.25 (two symmetric band groups, 8H; piperazine), 3.95 (s, 2H; Ar—CH$_2$—Ar), 7.2 (m, 8H, Ar—) and 12.5 (wide, 1H; —N$^+\overline{H}$—).

EXAMPLE 10

1-[4-Methyl-2-[(4′-methoxyphenyl)methyl]phenyl]piperazine hydrochloride 53.8 g of 2-(4′-methoxybenzyl)-4-methylaniline, 42.25 g of bis-(2-chloroethylamine)hydrochloride in 185 ml of n-butanol and repeated additions of 16.36 g of anhydrous potassium carbonate are reacted according to the method described in Ex. 1. The n-butanol is evaporated and the resulting resinous residue is stirred with 300 ml of toluene, and the hydrochloride is insolubilized as a white solid, which is then filtered off and dried; it weighs 19.25 g (25%), m.p. 180°–182° C., chromatographically pure. The toluene waters are concentrated at half volume and a second harvest impurified by the base is separated. The hydrochloride recrystallizes from ethanol to 75% yield, m.p. 183°–185° C. and analysis correct.

IR Spectrum (KBr), cm$^{-1}$: 3400, 3100–2440, 1620, 1520, 1250, 1190, 1050, 830.

$^1$H—NMR Spectrum (CDCl$_3$) ppm: 2.25 (s, 3H; CH$_3$—); 3.12 (two symmetric band groups, 8H; piperazine), 3.60 (s, 3H; —OCH$_3$), 8.25 (wide, 2H; —N$^+$H$_2$).

EXAMPLE 11

1-[4-Methyl-2-[(4′-methoxyphenyl)methyl]phenyl]-4-methylpiperazine hydrochloride From 5.0 g of 1-[4-methyl-2-[(4′-methoxyphenyl)methyl]phenyl]piperazine hydrochloride, 3.12 ml of 37% formaldehyde and 1.25 ml of formic acid, and operating as described in Ex. 2, 5.1 g of whitish solid are isolated, m.p. 195°–197° C. chromatographically pure and analysis correct.

IR Spectrum (KBr), cm$^{-1}$: 3450, 3040–2400, 1520, 1255, 1040, 1000, 865, 825.

$^1$H—NMR Spectrum (CDCl$_3$), ppm: 2.26 (s, 3H; CH$_3$—), 2.80 (s, 3H; N—CH$_3$), 3.18 (wide, 8H; piperazine), 3.75 (s, 3H; —OCH$_3$), 3.91 (s, 2H; Ar—CH$_2$—Ar), 6.7–7.2 (m, 7H; Ar—) and 9.6 (wide, 1$\overline{H}$; —N$^+$H).

EXAMPLE 12

1-[4-Chloro-2-[(2′-chlorophenyl)methyl]phenyl]piperazine hydrochloride 38.12 g of 2-(2′-chlorobenzyl)-4-chloroaniline, 28.23 g of bis-(2-chloroethylamine)hydrochloride in 150 ml of n-butanol and repeated additions of 10.51 g of anhydrous potassium carbonate are reacted according to the method described in Ex. 1. The n-butanol is evaporated and the resulting resinous residue dissolved in toluene is neutralized with 1N sodium hydroxide solution, washed with water, and the toluene (21 g) is evaporated. It is dissolved in ethanol. Hydrochloric acid gas is bubbled into this solution with cooling, and the hydrochloride precipitates; it is filtered, dried and recrystallized from isopropanol to give 8.15 g of end product, m.p. 171.5°–173° C. and analysis correct.

IR Spectrum (KBr), cm$^{-1}$: 3500, 3100–2400, 1590, 1480, 1450, 1240, 1110, 1050, 925, 740.

$^1$H—NMR Spectrum (d$_6$—DMSO), ppm: 3.08 (wide, 8H; piperazine), 4.12 (s, 2H; Ar—CH$_2$—Ar), 6.8–7.5 (m, 7H; Ar—) and 9.6 (wide, 2H; —N$^+$H$_2$—).

EXAMPLE 13

1-[4-Chloro-2-[(4'-methylphenyl)methyl]phenyl]piperazine hydrochloride 20.81 g of 2-(4'-methylbenzyl)-4-chlorocaniline, 16.03 g of bis-(2-chloroethylamine) in 85 ml of n-butanol and repeated additions of 6.13 g of anhydrous potassium carbonate are reacted according to method described in Ex. 1. The butanol layer is evaporated, taken up in toluene, made basic with 1N NaOH solution, washed with water and evaporated to dryness; it is then dissolved in 60 ml of ethanol. 15 ml of concentrated hydrochloric acid are added and the precipitate (starting aniline hydrochloride) is filtered off. The filtrate is evaporated, neutralized and dissolved in 90 ml of dry methylene chloride. Hydrochloric acid gas is bubbled into this solution with cooling, and the hydrochloride precipitates; after 24 hrs in the refrigerator, it is filtered, dried and recrystallized from methanol to give 7.87 g (26%) of end product, m.p. 216°–218° C., chromatographically pure and analysis correct.

IR Spectrum (KBr), cm$^{-1}$: 3500, 3100–2400, 1480, 1450, 1230, 1110, 1040, 820.

$^1$H—NMR Spectrum (d$_6$—DMSO), ppm: 2.25 (s, 3H; CH$_3$—), 3.08 (2ide, 8H; piperazine), 9.96 (s, 2H; Ar—CH$_2$—Ar), 7.2 (m, 7H; Ar—) and 9.75 (wide, 2H; —N$^+$H$_2$—).

We claim:

1. An 1-[2-phenylmethyl)phenyl]piperazine of the formula (I):

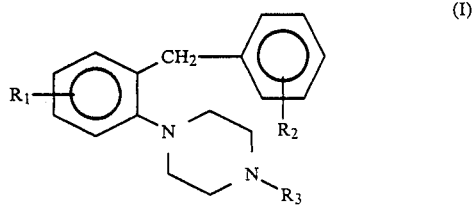

or a pharmaceutically acceptable acid addition salt thereof, wherein R$_1$ is hydrogen, C$_{1-4}$ alkylor halogen, R$_2$ is hydrogen, C$_{1-4}$ alkyl, halogen or C$_{1-4}$ alkoxy and R$_3$ is hydrogen or methyl.

2. The compound of claim 1: 1-[5-Methyl-2-(phenylmethyl)phenyl]piperazine.

3. The compound of claim 1: 1-[5-Methyl-2-(phenylmethyl)phenyl]piperazine monohydrochloride.

4. The compound of claim 1: 1-[5-Methyl-2-(phenylmethyl)phenyl]piperazine dihydrochloride.

5. A pharmaceutical composition comprising a compound of claim 1 in a therapeutically effective amount sufficient to act as an antidepressive with pharmaceuticallt acceptable additives.

* * * * *